(12) United States Patent
Cameron et al.

(10) Patent No.: US 8,845,100 B2
(45) Date of Patent: Sep. 30, 2014

(54) NON-INVASIVE OCULAR ANALYTE SENSING SYSTEM

(75) Inventors: Brent D. Cameron, Waterville, OH (US); Anthony Webb, Toledo, OH (US)

(73) Assignee: The University of Toledo, Toledo, OH (US)

( * ) Notice: Subject to any disclaimer, the term of this patent is extended or adjusted under 35 U.S.C. 154(b) by 283 days.

(21) Appl. No.: 13/500,706

(22) PCT Filed: Oct. 7, 2010

(86) PCT No.: PCT/US2010/051763
§ 371 (c)(1),
(2), (4) Date: May 2, 2012

(87) PCT Pub. No.: WO2011/044322
PCT Pub. Date: Apr. 14, 2011

(65) Prior Publication Data
US 2012/0268714 A1    Oct. 25, 2012

Related U.S. Application Data

(60) Provisional application No. 61/249,551, filed on Oct. 7, 2009.

(51) Int. Cl.
*A61B 3/10*    (2006.01)
*A61B 5/1455*    (2006.01)

(52) U.S. Cl.
CPC .................................. *A61B 5/14558* (2013.01)
USPC .......................................... 351/221; 351/246

(58) Field of Classification Search
USPC .......... 600/319, 316, 318, 322–326; 128/633, 128/664; 356/39, 40; 351/206, 246, 221
See application file for complete search history.

(56) References Cited

U.S. PATENT DOCUMENTS

| | | | | |
|---|---|---|---|---|
| 5,433,197 | A * | 7/1995 | Stark | 600/319 |
| 5,713,353 | A * | 2/1998 | Castano | 600/319 |
| 6,442,410 | B1 * | 8/2002 | Steffes | 600/319 |
| 7,438,855 | B2 * | 10/2008 | Sota et al. | 422/82.09 |
| 2005/0171416 | A1 * | 8/2005 | Proniewicz et al. | 600/319 |
| 2009/0240124 | A1 * | 9/2009 | Hefti | 600/319 |

* cited by examiner

*Primary Examiner* — Hung Dang
(74) *Attorney, Agent, or Firm* — MacMillan, Sobanski & Todd, LLC

(57) ABSTRACT

A noninvasive method and apparatus for determining analyte concentration (e.g., glucose) in a subject that includes measuring light refraction from at least a portion one or more structures. One example of such structure is the subject's iris.

98 Claims, 12 Drawing Sheets
(10 of 12 Drawing Sheet(s) Filed in Color)

NON-INVASIVE OCULAR ANALYTE SENSING SYSTEM

CROSS-REFERENCE TO RELATED APPLICATIONS AND STATEMENT REGARDING SPONSORED RESEARCH

The present invention claims the benefit of the PCT/US2010/051763 filed Oct. 7, 2010 which claims priority to the provisional patent application Ser. No. 61/249,551, filed Oct. 7, 2009. This invention was not made with any government support and the government has no rights in this invention.

BACKGROUND OF THE INVENTION

There is no admission that the background art disclosed in this section legally constitutes prior art.

Diabetes mellitus is a disease where individuals have difficulty regulating their blood glucose levels, in which extremely low or high glucose concentrations can occur. Normal physiological blood glucose ranges are generally between 80-120 mg/dL (milligrams per deciliter); however, diabetics commonly have blood concentrations from 50-500 mg/dL if not properly treated. The Center for Disease Control and Prevention estimates that approximately 23.6 million individuals have some form of diabetes mellitus in the United States. If diabetes is not properly treated, other complications such as heart disease, diabetic neuropathy, and kidney disease may also arise.

The disease is commonly divided into two types. Type I diabetes is characterized by an auto-immune response resulting in the destruction of the pancreatic beta cells responsible for the production of insulin (i.e., the hormone responsible for cellular glucose uptake). Therefore, Type I diabetics are completely dependent on therapeutic insulin to compensate for this loss. Type II diabetes is related to decreased insulin sensitivity. This causes an individual to secrete larger amounts of insulin to compensate; however, often the body can not produce the required amounts.

The key to treating diabetes through therapy is to frequently monitor blood glucose concentrations, such that corrective actions can be taken. This is normally accomplished though invasive approaches, in which the testing procedure requires the skin barrier to be broken in order to obtain a blood sample for analysis. These invasive methods, however, involve pain and increased risk of infection that commonly result in low compliance. Although, only invasive methods are currently approved by the Food and Drug Administration (FDA) for monitoring physiological glucose, many others are attempting to develop a noninvasive blood glucose sensor. While there are many approaches proposed for noninvasive glucose sensing, however, none to date have obtained FDA approval for this application.

SUMMARY OF THE INVENTION

In a first broad aspect, there in provided herein a noninvasive system, for determining concentration of glucose in a subject, comprising measuring at least light refraction from one or more fiducial markers in an eye of the subject.

In another aspect, there is provided herein a system, for determining concentration of glucose in a subject, comprising:

an energy source that emits at least one beam of non-collimated light, the beam being directed at one or more fiducial markers in the eye, such that at least a portion of the beam is refracted by the one or more fiducial markers; and, at least one data capturing module that receives at least one data point formed by the refracted beam, the data point comprising a perception of the one or more fiducial markers, and based on the perception, the data capturing module correlates a level of glucose in the eye with the one or more data points. The system can include obtaining two or more data points, either simultaneously or sequentially.

In certain embodiments, the fiducial marker of the eye comprises at least one of: an iris, a cornea, a corneal reflection, a sclera, a scleral reflection, and a pupil. Also, in certain embodiments, the fiducial markers comprise one or more of: crypts, ridges and furrows of the subject's iris.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A—Raw image of 0 mg/dL; FIG. 1B—Image of difference between 0 mg/dL and 0 mg/dL; FIG. 1C—Raw image of 3000 mg/dL; FIG. 1D—Image of difference between 0 mg/dL and 3000 mg/dL; FIG. 1E—Raw image of 6000 mg/dL; FIG. 1F—Image of difference between 0 mg/dL and 6000 mg/dL; FIG. 1G—Raw image of 9000 mg/dL; FIG. 1H—Image of difference between 0 mg/dL and 9000 mg/dL.

FIG. 5A—Image score plot for the first principal component for 0 and 100 mg/dL; FIG. 5B—Principal component 1 scores versus principal component 2 scores for 0 and 100 mg/dL; FIG. 5C—Image score plot for the first principal component for 0 and 500 mg/dL; FIG. 5D—Principal component 1 scores versus principal component 2 scores for 0 and 500 mg/dL; FIG. 5E—Image score plot for the first principal component for 0 and 1000 mg/dL; FIG. 5F—Principal component 1 scores versus principal component 2 scores for 0 and 1000 mg/dL.

DETAILED DESCRIPTION OF THE PREFERRED EMBODIMENT(S)

Figure 1A:
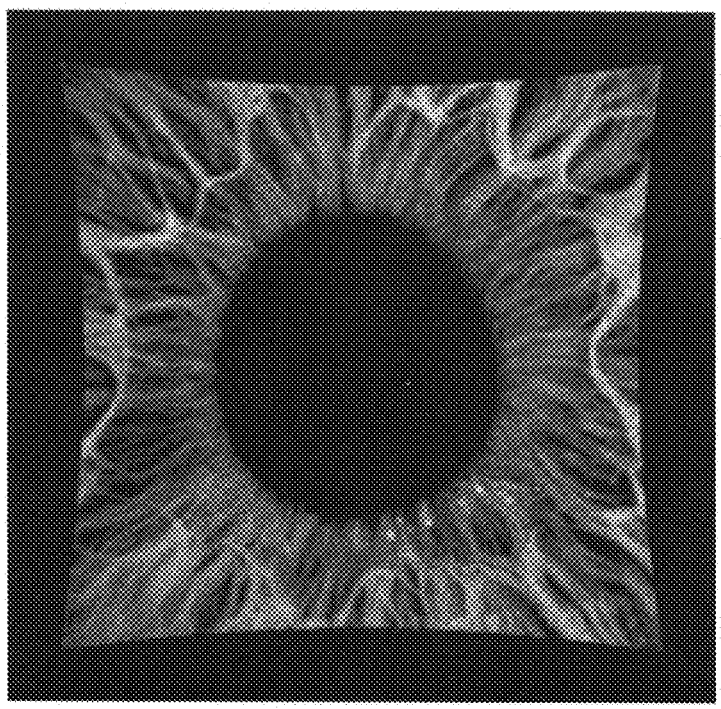
FIGS. 1A-1H.
Figure 1B:
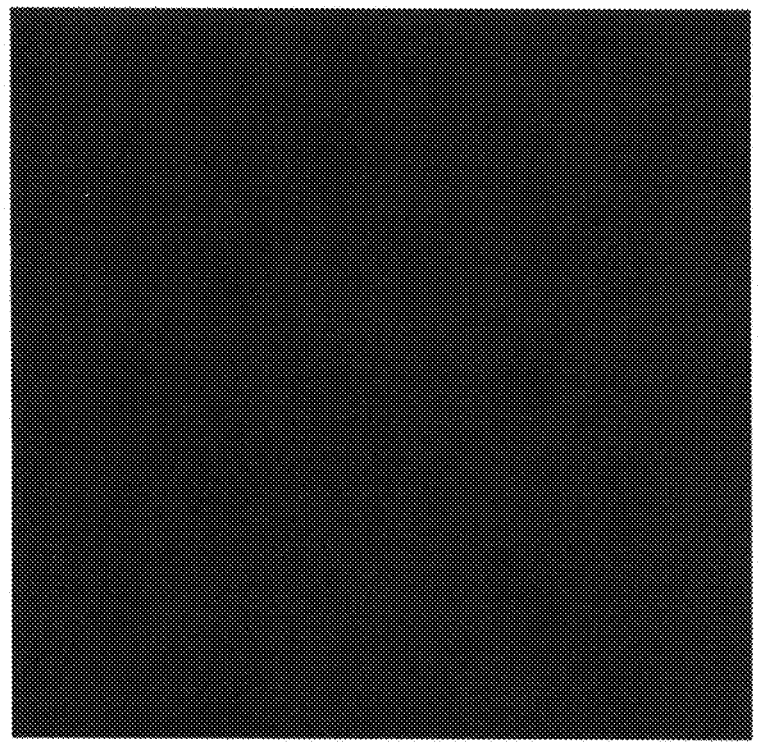
Figure 1C:
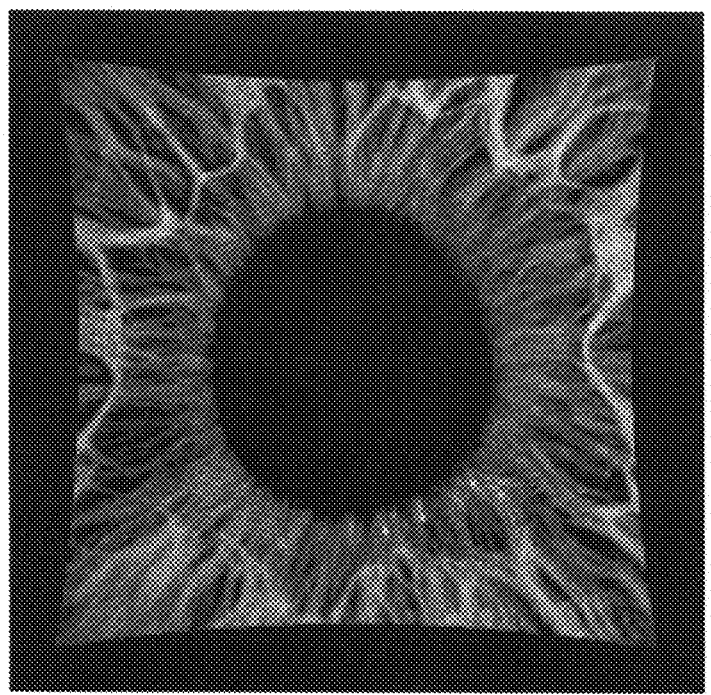
Figure 1D:
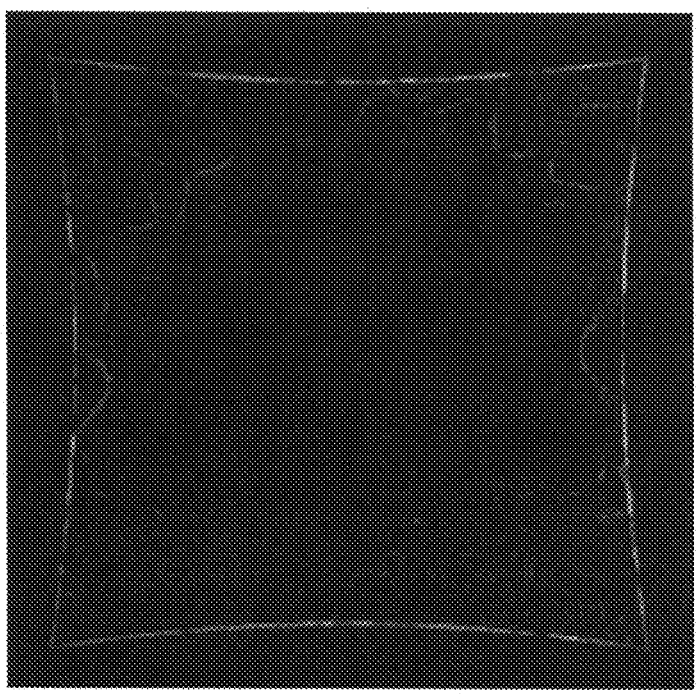
Figure 1E:
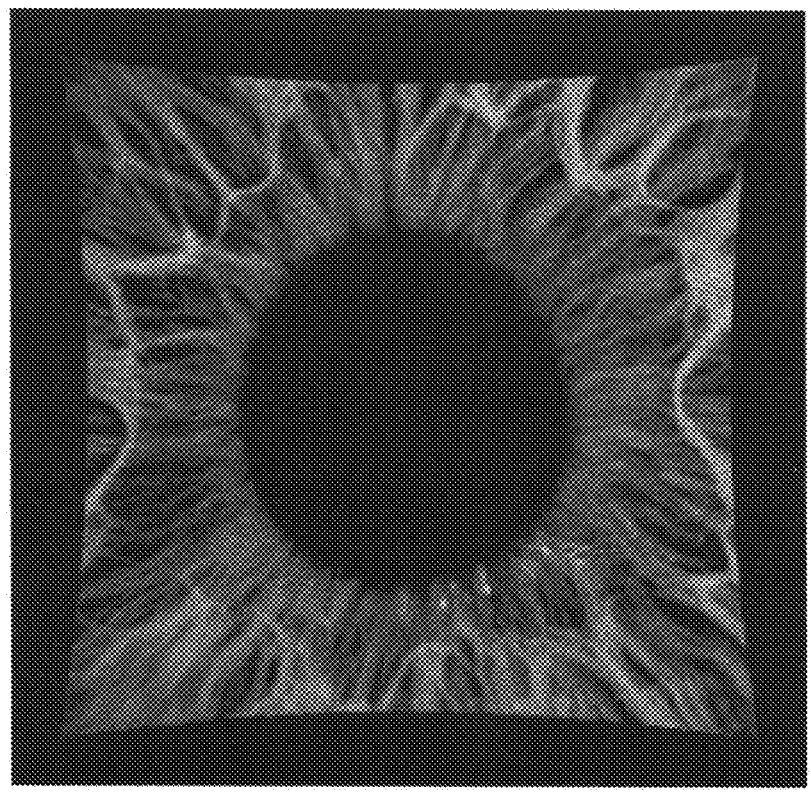
Figure 1F:
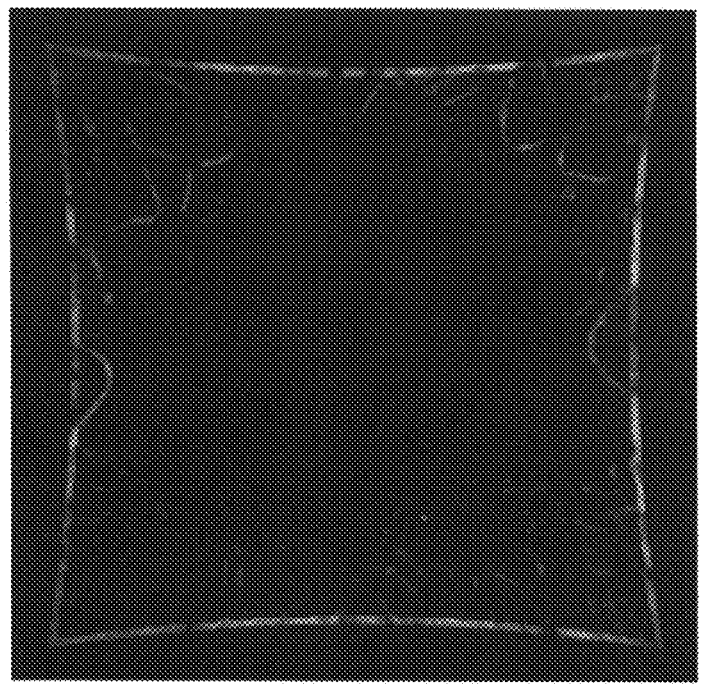
Figure 1G:
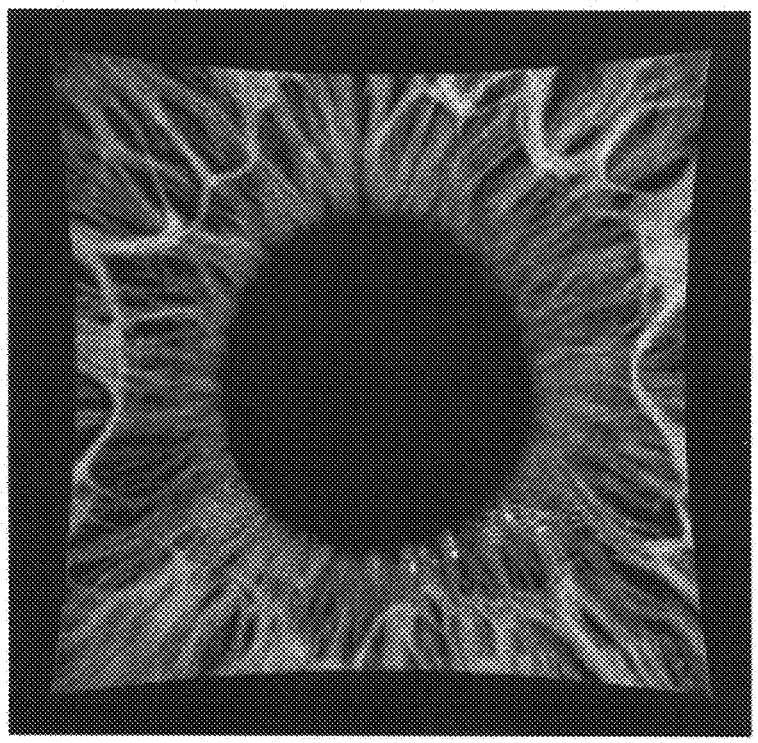
Figure 1H:
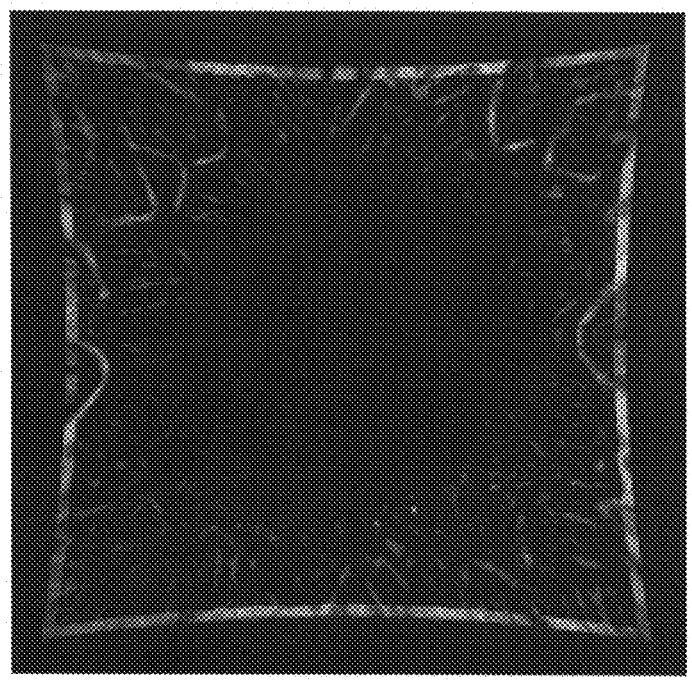

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Changes in glucose concentration will result in small variations in the optical refractive index of the aqueous humor of the eye (i.e., the clear fluid between the cornea and lens). This can directly affect the perception of the iris pattern through both scattering and refraction principles. The cornea is a transparent tissue which serves as the optical window into the eye. The cornea refracts the light towards the interior of the eye through the clear liquid known as the aqueous humor which is contained in the eye's anterior chamber. This fluid is a filtrate of the blood and is optically transparent. The aqueous humor also contains glucose levels that are directly correlated to those of blood. Located within the anterior chamber is the iris, which is responsible for limiting the amount of light entering the eye through the pupil. The iris contains specific structures such as crypts, ridges, and furrows which are extremely specific spatial markers that are examined and measured in the method described herein.

In a broad aspect, described herein are a method and apparatus for the noninvasive measurement of physiological glucose based on the ocular imaging and analysis of the iris of the eye.

The method described herein varies from optical coherence tomography (OCT) which collects backscattered coherent light from a tissue sample using an interferometeric based sensor. In OCT, the collected signal can also used to monitor changes in the refractive index mismatch within a tissue under evaluation. In OCT, the signal is generated based on optical scattering, and any changes in glucose concentration can then be related to the OCT signal. As glucose concentrations increase, the overall scattering would decrease. Although OCT has been demonstrated for use in glucose detection, a main disadvantage of OCT is its overall cost (~$30 k to $200 k). In addition, variations in tissue structure, even within an individual, can also prove problematic for OCT, especially in calibration. Both disadvantages hinder the development of OCT for commercial glucose sensing.

Experimental in vivo data shows that blood glucose levels correlate well with those of the aqueous humor with a time delay on the order of approximately 5 minutes. This minimal time lag is deemed acceptable in regards to the application of diabetic glucose sensing. Also, the refractive index of the aqueous humor changes with variations in glucose concentration; that is, a change of ~10 mg/dL of glucose corresponds to a refractive index change on the order of $1.4 \times 10^{-5}$. These data provide a basis for the method described herein where these data are coupled to the uniqueness of the iris structure and are utilized in the noninvasive ocular glucose sensor described herein.

Every iris has unique features, such as crypts, ridges, and furrows. These features, or fiducial markers, are used in the method described herein. As generally used herein a "fiducial marker" is a feature of the eye in the field of view of an imaging system which appears in the image produced, for use as a point of reference or a measure.

The present method correlates individual optical signals from one or more such fiducial markers to the optical refractive index of the aqueous humor; and thus, the glucose concentration.

In particular, the optical signals comprise refracted light from one or more of such fiducial markers.

If the glucose concentration changes, since the human iris has many fiducial markers, the perception of these markers/signals with respect to each other will also vary, or change.

In the method described herein one or more data points are collected, where such data points include one or more variations in the perception of the fiducial markers. These data points are calibrated around the glucose concentration of the subject. The method described herein provides an advanced and robust method that provides an accurate prediction of glucose in the physiological range.

The method described herein applies Snell's law to describe the refraction or bending of light with respect to the difference in the index of refraction between two given media, wherein, $$(\sin \theta_1)/(\sin \theta_2) = \eta_2/\eta_1, \text{ where} \qquad \text{Equation 1:}$$

$\eta_1$ is the refractive index of the primary (incident) medium,
$\eta_2$ is the refractive index of the secondary (transmitted) medium,
$\theta_1$ is the angle that the incident light rays take with respect to the normal, and
$\theta_2$ is angles that the light rays take with respect to the normal.

Therefore, if the refractive index changes with respect to one of the media, the corresponding angle will change (or the light will refract/bend). In the method herein, as incident light (generally comprised of a diverging beam of light) travels from one material to another, the light will refract, assuming different refractive indices.

As the aqueous humor glucose concentration varies, the refractive index will cause the numerous light rays to bend as they are reflected, or are backscattered, from the iris.

For example, one perception that can be measured by the method described herein is that the acquired iris image will appear to either contract inwardly or outwardly, depending on the change in glucose concentration. Other relationships among one or more perceptions that can be evaluated by the method described herein include, but are not limited to, comparing or correlating individual signals generated/reflected/backscattered by the iris.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

As supporting results, FIGS. 1A-1H are a series of sequence of raw and subtracted (all referenced from 0 mg/dL concentration) iris images that are utilized in an optical simulation containing different levels of ocular aqueous humor glucose concentration. The FIGS. 1A-1H illustrate that, for changes in glucose concentration, the acquired iris image will change due to the variations in the refractive indices due to changing glucose concentration. This is shown by the borders and iris features thickening in each sequential sub-figure. The larger glucose concentrations were only used in the simulations to facilitate the illustration of this effect. This spatial dependence and expansion/contraction of the iris patterns allows for the potential development and use of advanced multivariate image analysis methods to be effective at detecting physiological glucose levels related to minute changes of the refractive index.

In vitro iris simulations were completed using three dimensional optical ray tracing software. A realistic eye model along with a supporting imaging method was created as a 3D based CAD model with all optical parameters defined. The optical properties used were based on the real world values for both the cornea, aqueous humor, as well as other eye structures. The iris structure is based off an actual human iris image. The aqueous humor was initially given a refractive index value of 1.33 and was subsequently varied by increments of $1.4 \times 10^{-5}$ up to 1.3314. This corresponded to the glucose ranges of 0 mg/dL to 1000 mg/dL by increments of 100 mg/dL.

Figure 2:
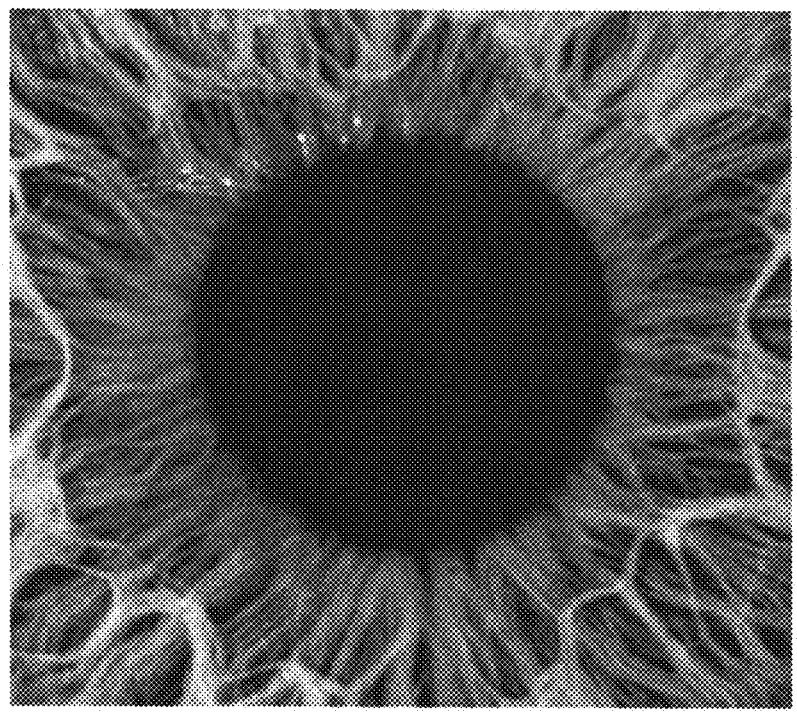
FIG. 2: Human iris image used as in the ray tracing simulations.

The ray tracing was completed using the incorporated realistic human iris image as shown in FIG. 2. This iris image was placed in the position where the iris would be located in the optical ray tracing model which is directly behind the anterior chamber (between the lens and cornea). This image was treated as a source within the ray tracing simulation so that each pixel would irradiate a ray giving a total of 500,000 rays per wavelength of 460 nm, 540 nm, and 620 nm at each glucose concentration. This is essentially the same as using an external illumination source directed onto the iris before the light is backscattered toward the camera.

The acquired images corresponding to each glucose concentration were then subsequently post-processed using digital image filtering techniques. This allowed for selection and enhancement of distinct iris features, while minimizing background noise for the imaged based extension of principal component analysis (PCA) and partial least squares (PLS) regression techniques. This analysis provided the capability to perform a score analysis on the set of images as well as performing multivariate image regression (MIR).

The MIR was performed using a PLS algorithm in order to form a calibration model that is capable of predicting a glucose concentration given an iris image. In order to validate the calibration model, cross validation was used to assess how well the predictive model could estimate glucose concentrations on unseen data sets. The score analysis was then used in order to better understand the regression model generated by the PLS approach and provided significant insight into the characteristics of the generated signals.

Figure 3:
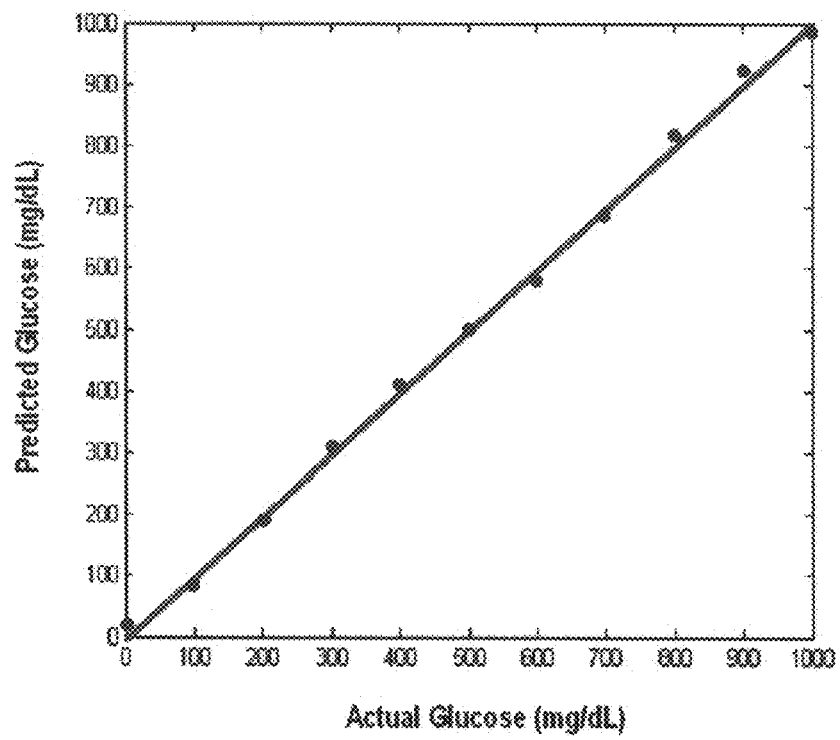
FIG. 3: Glucose concentration estimation results in mg/dL calibration.
Figure 4:
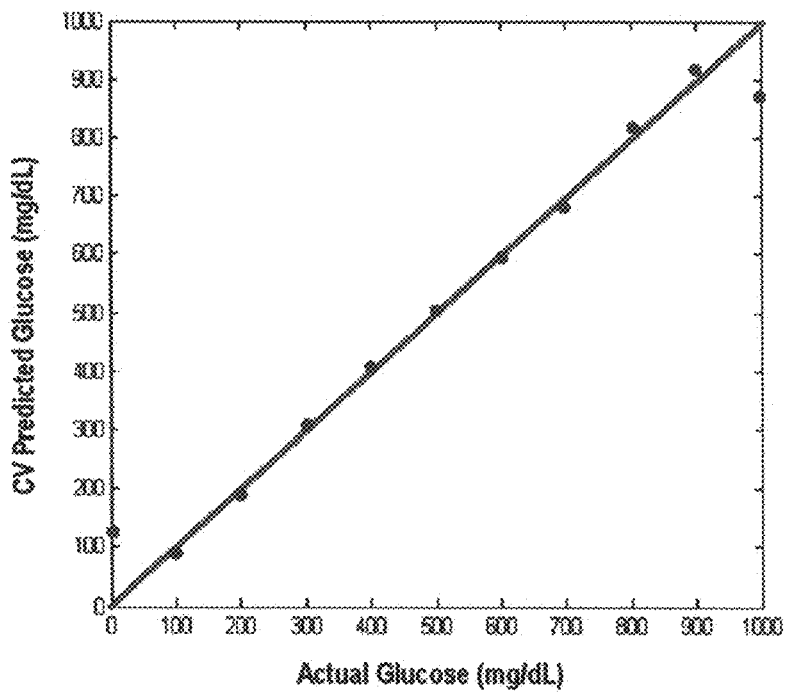
FIG. 4: Glucose concentration estimation results in mg/dL cross validation.

The resulting calibration and cross validation plots are shown in FIGS. 3-4. As shown within the FIGS. 3-4, the estimated physiological glucose concentrations for both the calibration and cross validation are highly correlated with correlation coefficients of 0.998 and 0.976, respectively. In addition to the correlation coefficients, the standard errors of calibration and cross validation were calculated to be 1.5% and 5.4%, respectively. The cross validation error is expected to be higher due to the fact that the calibration model is being used for an unseen data set however; both error values are well within acceptable physiological sensing limits.

To analyze the detected signals exploited in the use of the PLS approach, thus allowing for the accurate prediction of physiological glucose, the method of principal component analysis was applied to the acquired image dataset. The score plots shown in FIGS. 5A-5F display a sequence of both: the image scores for first principal component, and also the score plots of the first versus the second principal components from the image data resulting from the ray tracing simulations (details on the respective glucose concentrations are provided within the figure caption).

Figure 5A:
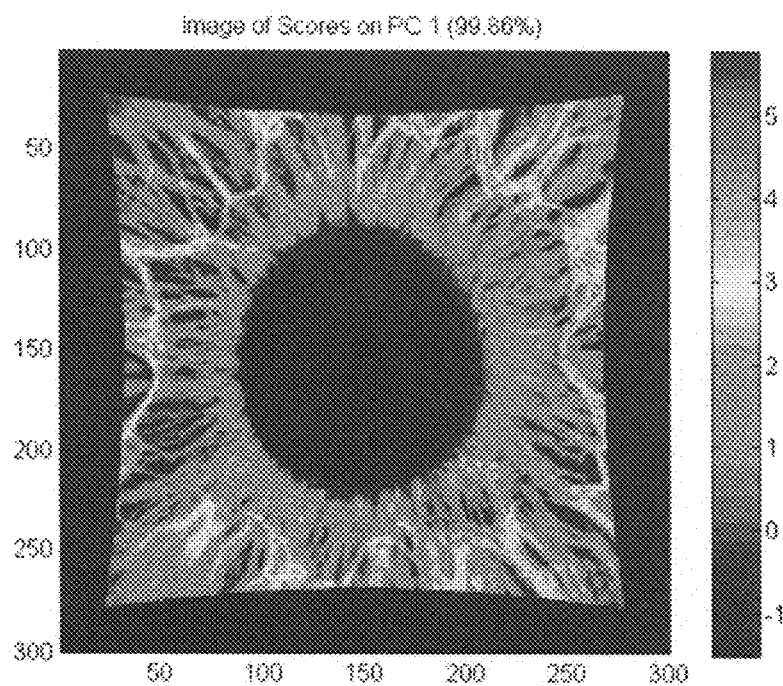
FIGS. 5A-5F.
Figure 5B:
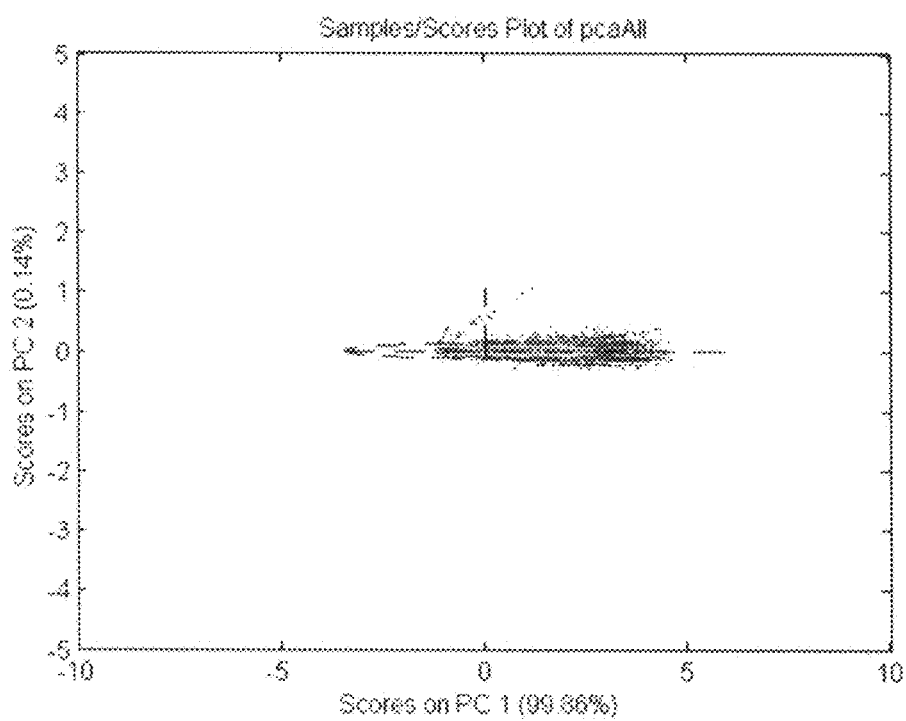
Figure 5C:
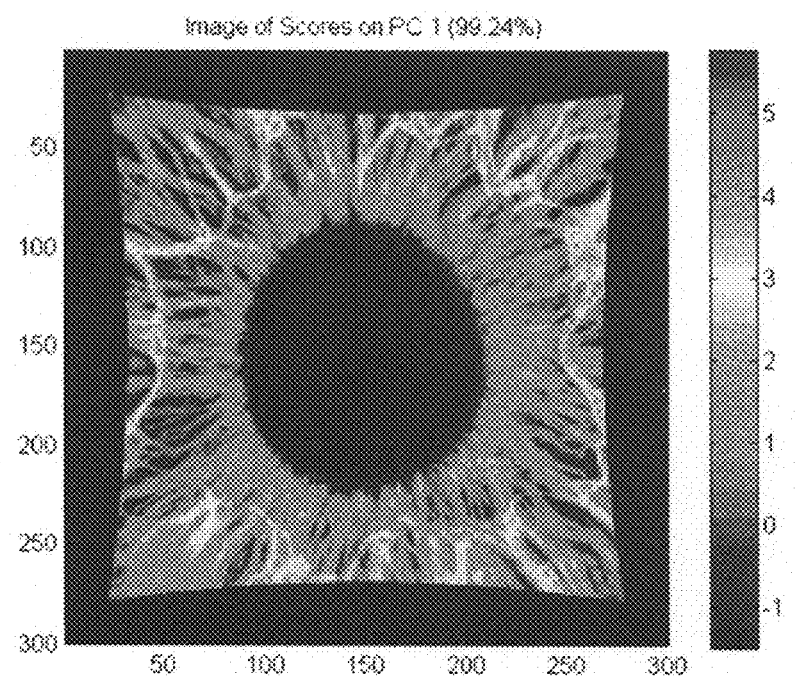
Figure 5D:
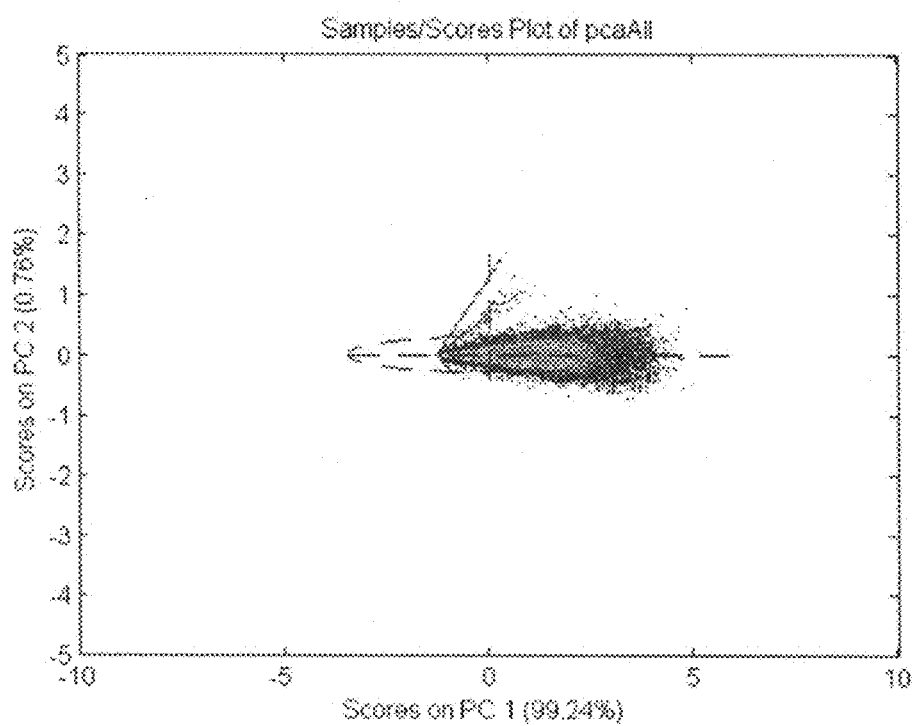
Figure 5E:
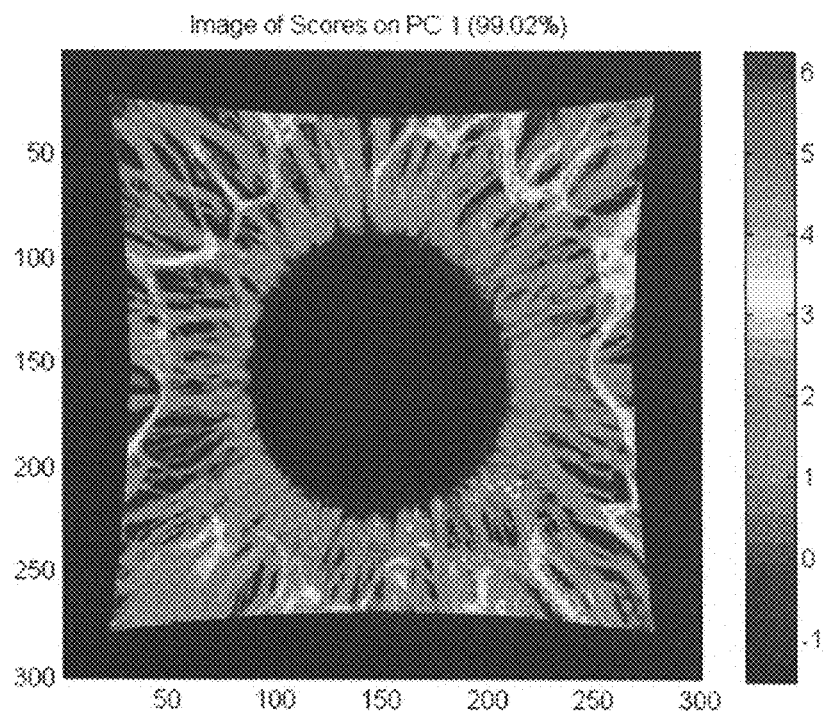

FIG. 5A, FIG. 5C, and FIG. 5E show the scores of the first principal component in a pseudo red, green, and blue color space. When the glucose concentration is increased, the areas with high spatial variability begin to decorrelate due perception changes related to the refractive index/glucose concentration. As can be seen in these images, the amount of variance or score levels within these images begins to decrease (e.g., 99.86%, 99.24%, and 99.02% for glucose concentrations of 100, 500, and 1000 mg/dL, respectively, compared to 0 mg/dL). These phenomena essentially detail the signal factors exploited by the developed image-based regression algorithm which allows for estimation of glucose concentration in the physiological range.

Figure 5F:
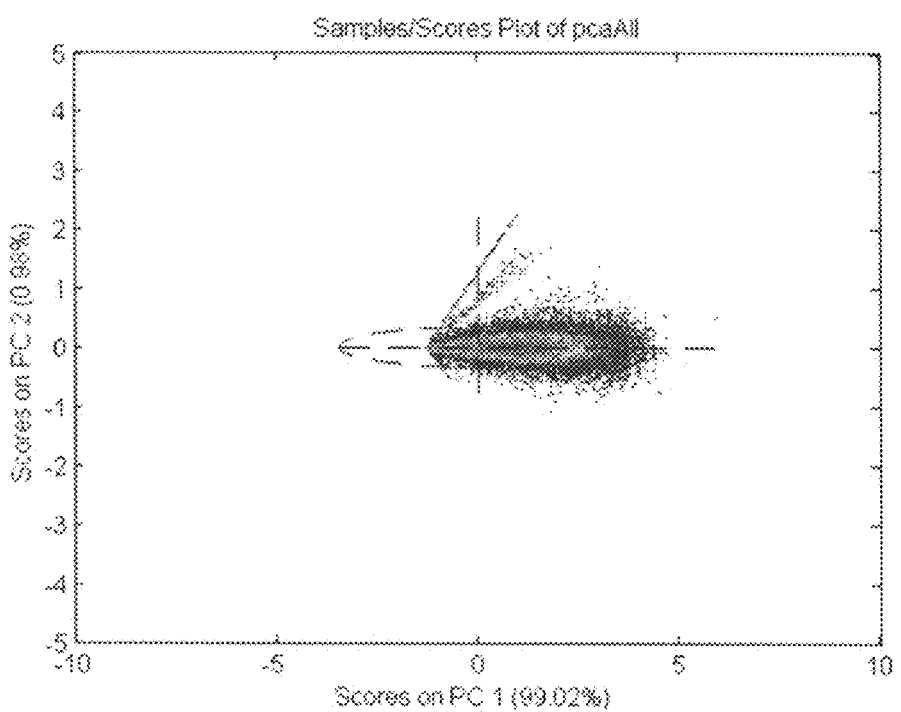

The ellipsoid shapes of FIG. 5B, FIG. 5D, and FIG. 5F show that relationships between the two differing concentrations are captured within the first and second principal components. Thus, when comparing an image at one concentration with respect to another, the similarity between the two images is represented in first component (major axis of the ellipse) while the second component shows where the main dissimilarities occur (minor axis of the ellipse). As can be seen from the plots in FIGS. 5A-5F, an increase in the glucose concentration causes the minor axis of the ellipse to increase (or the scores of second principal components to increase with respect to the first) signifying a direct correlation to an increase in the refractive index and thus glucose concentration. Another way of interpreting this effect, is that as glucose concentration increases, a portion of the variance captured within the first principal component is transferred to the second principal component. The magnitude of the amount of variance which is transferred is therefore related to glucose concentration.

In Vivo Measurements

The in vivo implementation of the method described herein can be configured to be sufficiently robust to adapt to physiological responses.

The method can use a suitable sequential imaging technique that is accompanied with a physiological calibration process.

In one non-limiting example, the method can include a bimodal light source with both stimulus and illumination wavelengths. The stimulus wavelength can be located in the blue-green region in order to maximize the pupillary light reflex of the human eye due the enhanced retinal sensitivity for that wavelength range. By using the stimulus source at varying intensities, the method described herein compensates for the spatial variations in the iris pattern due to an increase or decrease in the pupil diameter. The measured compensation is dynamically encoded into the regression technique, such as, with a partial least squares (PLS) calibration approach as an example.

In the method describe herein, this extended utilizes dynamic image data compared to static data. For example, at a given concentration, instead of each glucose concentration being related to a static image, $I(x,y)$, the calibration data in the dynamic sense relates glucose concentration to a dynamic image, $I(x,y,t)$, where t is time. In essence, the dependent variable data are the respective movies of the eye response to the light protocol which correspond to a given glucose concentration.

The present method thus resolves any prediction issues associated with acquiring measurements at different light levels, which also have dependent iris/pupillary responses.

The method described herein can be generalized by a dynamic regression model, where $$C = I(x,y,t)B + B_0, \text{ wherein} \qquad \text{Equation 2:}$$

C is glucose concentration,

I is the dynamic image (i.e., movie or image sequence), and

B and $B_0$ are the respective regression parameters.

Figure 6:
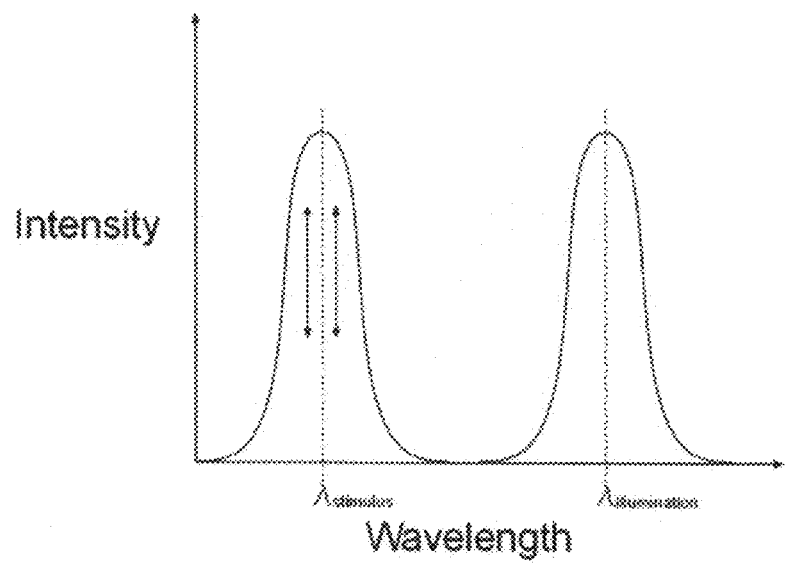
FIG. 6: Graph showing the biomodal spectral response of the light source.
Figure 7:
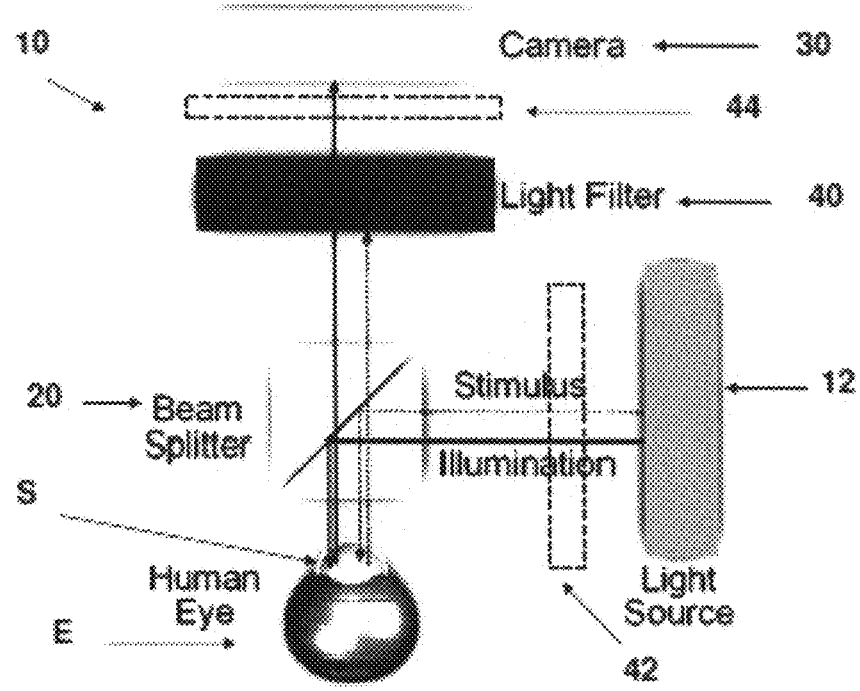
FIG. 7: Schematic illustration of one embodiment of an apparatus for in vivo based measurements.

In certain embodiments, the illumination source can be in the near infrared light region compared to the stimulus wavelength in the visible region (see FIG. 6). Using the near infrared region can also minimize corneal reflections to further enhance the iris structures thus increasing the signal-to-noise ratio. The illumination source can have a uniform irradiance profile in order to minimize light intensity variations across the image in order to optimize the acquired image quality. An example of how frontal illumination and stimulation can be combined is shown in FIG. 7.

Figure 8:
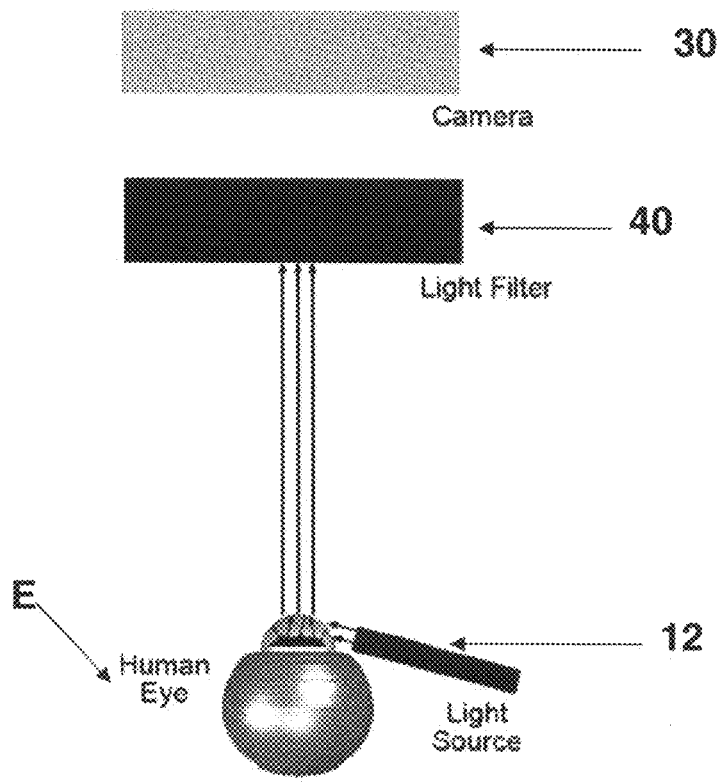
FIG. 8: Schematic illustration of another embodiment of an apparatus for in vivo based measurements.
Figure 10:
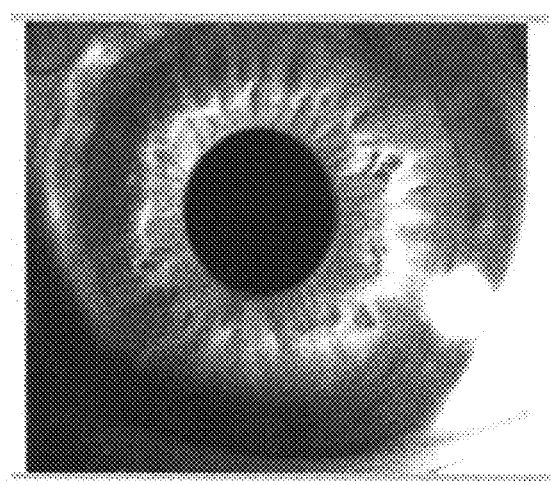
FIG. 10: Representative iris image taken with human based glancing angle configuration.

Further, the illumination and stimulation sources can be provided through a glancing angle approach, as shown in FIG. 8. In this approach, the ability to uniformly illuminate the anterior chamber of the eye can be accomplished as well as minimize light intensity variations across the image. This approach can significantly enhance the iris image and various structures. An example of this type of illumination for a human iris is shown in FIG. 10. Thus, in certain embodiments, the system for determining concentration of glucose in a subject, can generally include:

an energy source that emits at least one beam of non-collimated light, the beam being directed at one or more fiducial markers in the eye, such that at least a portion of the beam is refracted by the one or more fiducial markers; and, at least one data capturing module that receives at least one data point formed by the refracted beam, the data point comprising a perception of the one or more fiducial markers, and based on the perception, the data capturing module correlates a level of glucose in the eye with the one or more data points.

In certain embodiments, the data points comprise at least two images; and/or a substantially continuous, or movie, image. Further, in certain embodiments, at least a first data point is obtained at a first point in time, and wherein at least a second data point is obtained at a second point in time; and wherein the data capturing module compares the first data point to at least the second data point. Also, substantially the same fiducial marker can be evaluated. Further, the sequentially obtained data points are obtained over a defined period of time. The data capturing module can analyze one or more fiducial makers using each sequential data points.

The system can also include determining one or more of: spatial dependence and expansion/contraction in the eye.

The system can include relating one or more data points to a pre-determined calibration model to predict glucose concentration. Also, the data points can comprise image perception.

The system can also include determining a change in glucose concentration in the subject by relating a change in one or more acquired data points to the concentration of the glucose. In certain embodiments, the change comprises an expansion or contraction due to a change in the refractive index of one or more of the fiducial markers.

The system can also include analyzing one or more data points using a multivariate image analysis process. In certain embodiments, the system can include using an advanced multivariate image analysis to relate multiple backscattered signals to detect minute changes of refractive index. Also, one or more acquired data points can be selected and/or enhanced, while minimizing background noise and/or motion artifact.

The system can also include analyzing one or more data points using an imaged based principal component analysis (PCA) and/or partial least squares (PLS) regression method In certain embodiments, two or more acquired data points are compared using a correlation and/or differencing method.

The system can include performing a score analysis on multiple data points as well as utilizing multivariate image regression (MIR). In certain embodiments, the system can comprise performing MIR using a PLS or other suitable algorithm in order to form a calibration model that is capable of predicting analyte concentration.

Also, the system can include using a multivariate algorithm for prediction of a concentration of glucose in both calibration and cross validation. In certain embodiments, the system can include using a multivariate algorithm based on one or more fiducial markers from one or more ocular structures of the eye.

For example, the system can comprise applying a principal component analysis to an acquired dataset comprised of at least two data points determined by analyzing one or more fiducial markers in an eye of the subject.

In another example, the system can comprise: i) analyzing first and second principal components of at least one dataset of the data points, and ii) analyzing score plots of the first versus the second principal components from the dataset, wherein a shape or perception changes show that concentration relationships are captured within the first and second principal component factors. In certain embodiments, the system can further include: comparing at least one data point at one concentration with respect to another, and determining whether the similarity between the two data points is represented in the first component, while the second component shows where main dissimilarities occur.

It is to be understood that a bimodal light source can be configured to generate at least one stimulus wavelength of light and at least one illumination wavelength of light, wherein the stimulus wavelength is in the visible to near-infrared region of the electromagnetic spectrum. The stimulus light energy can be generated at varying intensities, in order to compensate for any spatial variations in the subject's iris pattern due to an increase or decrease in the pupil diameter. In certain embodiments, the light source can be configured to provide a defined opto-stimulus protocol in which the stimulus light intensity is varied. Also, the compensation can be encoded into a partial least squares (PLS) calibration measurement.

The illumination source can have a uniform irradiance profile sufficient to minimize light intensity variations and to optimize the quality of the acquired images. Also, the light source can be configured to utilize optical powers in the microwatt range. In certain embodiments, the light source can comprise one or more light-emitting diodes (LEDs) or other suitable devices In certain embodiments, the illumination source can generate light in the near infrared light region (~700-1400 nm) to minimize corneal reflections and enhance the iris structures, and to increase the signal-to-noise ratio as scattering effects are also lessened.

It is also to be understood that the data capturing module can an image capturing device, such as camera configured to capture moving images, and/or a camera configured to capture still images.

The data capturing module can be configured to acquire a first moving image, or "movie," of the fiducial marker while following a defined opto-stimulus protocol in which the stimulus light intensity is varying while glucose concentration remains relatively unchanged. In certain embodiments, the opto-stimulus protocol causes the iris to either contract or expand, depending on the light level. Also, the data capturing module can be configured to obtain subsequent movie images at varying glucose levels, whereby a robust multivariate data set of data points at differing stimulus light intensity values and varying glucose concentrations are obtained.

Thus, by an iterative process of obtaining subsequent movie images at varying glucose concentrations, a robust dynamic multivariate data set of data points at differing stimulus light intensity values and varying analyte concentrations can be obtained and used for calibration.

The data capturing module can also be configured to obtain one or more supplemental data including, but not limited to: pupil diameter, iris characteristics, and/or cross correlation values prior to glucose calibrations. The supplemental data can be used to aid in obtaining accurate predictions of glucose concentrations.

The illumination source can be a substantially uniform irradiance profile to minimize light intensity variations across the image to optimize the acquired image quality. Also, the illumination source can be in the near infrared light region compared to the stimulus wavelength in the visible region. For example, the system can use the near infrared region to minimize corneal reflections to further enhance the iris structures, thus increasing the signal-to-noise ratio.

It is further to be understood that, in certain embodiments, the system can further include at least one beam splitter, wherein the light source and the beam splitter are configured: i) to direct at least one exiting beam of light from the light source to the beam splitter; and, ii) to reflect the exiting beam towards at least a portion of structure. Further, in certain embodiments, the system can further include at least one beam splitter, wherein the light source, beam splitter and data capturing module are configured such that one or more of the reflected/backscattered light passes back through the beam splitter toward the data capturing module.

One or more light filters can be used to remove the stimulus wavelength of the backscattered/reflected light, while allowing the illumination wavelength to pass, thereby optimizing the image quality. For example, the light filter can comprise: a notch filter with center wavelength of $\lambda_{stimulus}$, a band pass filter with a center wavelength of $\lambda_{illumination}$, or a combination of short and/or long-pass filters to propagate the illumination wavelength(s), $\lambda_{illumination}$, toward the data capturing device, while blocking the stimulus wavelength(s), $\lambda_{stimulus}$.

In another aspect, there is provided herein an in vivo method for measuring a physiological concentration of at least glucose in an eye of a subject, comprising measuring at least light refraction from one or more fiducial markers in an eye of the subject using a sequential imaging method that is accompanied with a physiological calibration process.

The bimodal light source can be used with both stimulus and illumination wavelengths. At least one stimulus wavelength of light energy can be used in order to maximize the subject's pupillary light reflex. A stimulus source of light can be used varying intensities in order to compensate for spatial variations in the iris pattern due to an increase or decrease in the pupil diameter. In certain embodiments, the measured compensation can be dynamically encoded into a suitable regression technique, such as, with a partial least squares (PLS) calibration approach. Also, the system can include using dynamic image data and/or static image data.

It is to be understood that the system can include using, at a given concentration, instead of each concentration being related to a static image, $I(x,y)$, the calibration data in the dynamic sense relates the concentration to a dynamic image, $I(x,y,t)$, where t is time. In certain embodiments, the dependent variable data are respective movies of the eye response to the light protocol which correspond to a given concentration.

Also, the system can include using a PCA/PLS type-model to include a dynamic aspect which includes a time-changing stimulus as a factor. For example, the system can include detecting correlated movements that are caused by time lags or delays that cannot be seen in a static calibration model.

Referring again to FIG. 7, there is a schematic illustration of various components and light propagation directions. As shown in FIG. 7, an apparatus 10 includes at least one light source 12. Non-limiting examples of light sources 12 provide an ultra-low power ($\mu W$) and utilize a light source such as light-emitting diodes (LEDs). The light source 12 integrates both the described stimulus wavelengths and the illumination wavelengths. An exiting beam encounters a beam splitter 20 and is reflected downward towards the human eye E. The beam contacts the eye iris and reflections/backscattering from the human eye iris structure S pass back through the beam splitter 20 toward a data capturing module 30, such as image capturing device (e.g., a camera).

It is to be understood, however in certain embodiments, prior to encountering the camera 30, a light filter 40 can be used to remove the stimulus portion of the backscattered/reflected light, while allowing the illumination light to pass, thereby optimizing the image quality. In non-limiting examples, the light filter can be either be a notch filter with center wavelength of $\lambda_{stimulus}$, or a band pass filter with a center wavelength of $\lambda_{Illumination}$.

In the configuration shown in FIG. 7, the camera 30 can acquire a first moving image, or "movie," of iris images while following a defined opto-stimulus protocol in which the stimulus light intensity is varying while glucose concentration remains relatively unchanged. The opto-stimulus causes the iris to either contract or expand, depending on the light level.

In addition, by iterating the previous process of obtaining subsequent movie images at varying glucose levels, a robust dynamic multivariate data set of iris images at differing stimulus light intensity values and varying glucose concentrations can be obtained and used for calibration.

In certain embodiments, the data set can be supplemented with one or more perceptions of such additional fiducial markers, such as, but not limited to: pupil diameter, iris characteristics, and/or cross correlation values prior to glucose calibration. In certain embodiments, such supplemental data can be used to aid in obtaining accurate predictions.

In another example, the method includes using a PCA/PLS type-model to include a dynamic aspect which includes a time-changing stimulus as a factor. Such method allows for the detection of correlated movements in the data that are caused by time lags or delays that cannot be seen in a static calibration model.

In another embodiment, the apparatus in FIG. 7 can be supplemented through the addition of one or more polarization controllers (i.e., a device capable of controlling or analyzing different states of optical polarization, such as, a linear polarizer, a polarizer and waveplate(s), a polarizer and variable retarder, a polarizer and Faraday component, a polarizer and photoelastic modulator, or similar combination). For example, a first controller can be placed between the light source 12 and the beam splitter 20 (i.e., location 42), while a second controller can be placed between the camera 30 and the light filter 40 (i.e., location 44).

Another example is shown in FIG. 8, which schematically illustrates various components and light propagation directions which incorporates a glancing angle illumination approach to the iris.

Figure 9A:
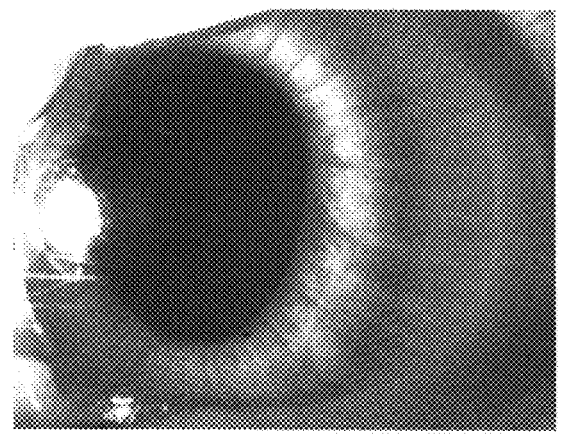
FIG. 9A: in vivo results acquired using a NZW rabbit animal model.
Figure 9B:
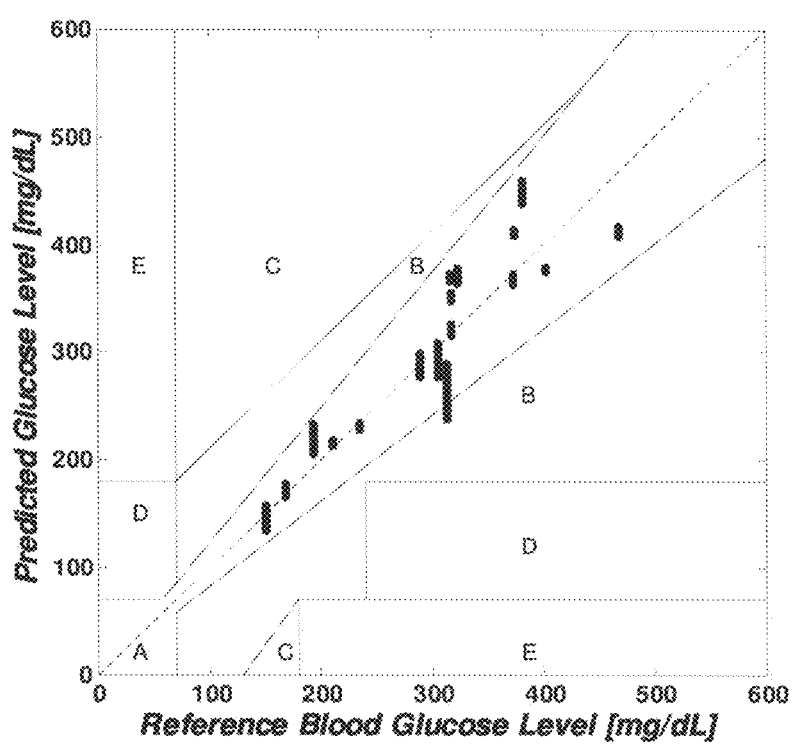
FIG. 9B: Corresponding blood glucose prediction reporting using a Clarke Error Grid.

In one embodiment, to form a working imaged based calibration model, multiple images can be taken as different physiological glucose levels are acquired. FIG. 9A is a representative rabbit iris image that is collected by the present method. The validation predictions using multiple images are shown in Clarke Error Grid format in FIG. 9B.

FIG. 10 is a representative human iris image taken using a glancing angle approach of the incident light on the iris. With the use of the glancing angle incident light, considerable enhancement in certain iris structures can be obtained as compared to a head-on illumination of the iris.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A system for determining concentration of an ocular analyte in a subject, comprising:
   an illumination source that emits at least one beam of non-collimated light, the beam being directed at one or more fiducial markers in the eye, such that at least a portion of the beam scattered or reflected by the one or more fiducial markers is refracted upon exiting the eye, wherein the illumination source has a glancing angle delivery; and,
   at least one data capturing module that receives at least one data point formed by the refracted beam, the data point comprising a perception of the one or more fiducial markers, and based on the perception of the one or more fiducial markers, the data capturing module correlates a level of ocular analyte in the eye with the one or more data points.

2. The system of claim 1, wherein the one or more fiducial markers comprises at least one of: an iris, a cornea, a corneal reflection, a sclera, a scleral reflection, and a pupil.

3. The system of claim 1, wherein two or more data points are obtained over time while concentration of the ocular analyte remains relatively unchanged, and the two or more data points comprise a substantially continuous series of points, movie, or images.

4. The system of claim 3, wherein at least a first data point is obtained at a first point in time, and wherein at least a second data point is obtained at a second point in time; and wherein the data capturing module compares the first data point to at least the second data point.

5. The system of claim 4, wherein the same fiducial marker is evaluated.

6. The system of claim 1, wherein the data points comprise at least two images.

7. The system of claim 1, wherein sequentially obtained data points are acquired over a defined period of time, and a dynamic calibration model is created from the sequential data points.

8. The system of claim 7, wherein the data capturing module analyzes one or more fiducial makers using each sequential data point.

9. The system of claim 1, wherein the data points include one or more of: spatial dependence and/or perception of expansion/contraction in the eye or eye structures.

10. The system of claim 1, wherein the correlation comprises determining a change in ocular analyte concentration in the subject by relating a change in one or more acquired data points to the concentration of the ocular analyte.

11. The system of claim 10, wherein the change comprises an expansion or contraction due to a change in the refractive index of one or more of the fiducial markers.

12. The system of claim 1, the at least one data point being analyzed using a multivariate image modeling or analysis process.

13. The system of claim 1, wherein the data capturing module comprises an image capturing device.

14. The system of claim 13, wherein the image capturing device comprises a camera configured to capture moving images.

15. The system of claim 13, wherein the image capturing device comprises a camera configured to capture still images.

16. The system of claim 1, wherein the light source is configured to utilize optical powers in the microwatt range.

17. The system of claim 16, wherein the light source comprises one or more light-emitting diodes (LEDs).

18. The system of claim 1, further including at least one beam splitter, wherein a stimulation source and the beam splitter are configured: i) to direct at least one exiting beam of light from the light source to the beam splitter; and, ii) to reflect the exiting beam towards the eye to stimulate a pupillary reflex.

19. The system of claim 1, further including at least one beam splitter, wherein the illumination source, beam splitter, and data capturing module are configured such that reflected or backscattered light resulting from the glancing angle illumination passes through the beam splitter toward the data capturing module.

20. The system of claim 1, wherein the data capturing module is configured to acquire a first moving image, or "movie," of the fiducial marker while following a defined opto-stimulus protocol in which the stimulus light intensity is varying while ocular analyte concentration remains relatively unchanged.

21. The system of claim 20, wherein the opto-stimulus protocol causes the iris to either contract or expand, depending on the light level.

22. The system of claim 1, wherein the data capturing module is configured to obtain subsequent movie images at varying ocular analyte levels, whereby a robust multivariate data set of data points at differing stimulus light intensity values and varying ocular analyte concentrations is obtained.

23. The system of claim 1, wherein the data capturing module is configured to obtain one or more supplemental data selected from: pupil diameter, iris characteristics, and cross correlation values prior to ocular analyte calibrations.

24. The system of claim 23, in which the supplemental data are used to aid in obtaining accurate predictions of ocular analyte concentrations.

25. The system of claim 1, wherein the ocular analyte comprises glucose.

26. A system for determining concentration of an ocular analyte in a subject, comprising:
   a bimodal illumination source that emits at least one beam of non-collimated light, the beam being directed at one or more fiducial markers in the eye, such that at least a portion of the beam scattered or reflected by the one or more fiducial markers is refracted upon exiting the eye, wherein the bimodal illumination source has a uniform irradiance profile and frontal delivery with both stimulus and illumination wavelengths; and at least one data capturing module that receives at least one data point formed by the refracted beam, the data point comprising a perception of the one or more fiducial markers, and based on the perception of the one or more fiducial markers, the data capturing module correlates a level of ocular analyte in the eye with the one or more data points.

27. The system of claim 26, wherein the one or more fiducial markers comprise one or more of: crypts, ridges and furrows of the subject's iris.

28. The system of claim 26, wherein two or more data points are obtained over time while concentration of the ocular analyte remains relatively unchanged, and the two or more data points comprise a substantially continuous series of points, movie, or images.

29. The system of claim 26, further including one or more light filters configured to remove the stimulus wavelength of reflected or backscattered light, while allowing the illumination wavelength to pass, thereby optimizing the image quality.

30. The system of claim 29, wherein the light filter comprises: a notch filter with center wavelength of $\lambda_{stimulus}$, a band pass filter with a center wavelength of $\lambda_{Illumination}$, or a combination of short and/or long-pass filters to propagate the illumination wavelength, $\lambda_{Illumination}$, toward the data capturing device, while blocking the stimulus wavelength, $\lambda_{stimulus}$.

31. The system of claim 26, wherein the stimulus and illumination wavelengths are different.

32. The system of claim 26, wherein the stimulus and illumination wavelengths are the same.

33. The system of claim 26, wherein the bimodal illumination source comprises varying intensities.

34. A method for determining concentration of an ocular analyte in a subject comprising:
    delivering an incident light from a bimodal light source having both stimulus and illumination wavelengths to at least a portion of the subject's eye, and
    measuring refraction of the incident light with respect to a change in an index of refraction of two given media related to Equation I, $(\sin \theta_1)/(\sin \theta_2)=\eta_2/\eta_1$, wherein
        $\eta_1$ is the refractive index of the primary (incident) medium,
        $\eta_2$ is the refractive index of the secondary (transmitted) medium,
        $\theta_1$ is the angle that the incident light rays take with respect to the normal, and
        $\theta_2$ is angles that the light rays take with respect to the normal.

35. The method of claim 34, further including determining the refractive index changes with respect to one of the media.

36. The method of claim 34 including relating one or more data points to a pre-determined calibration model to predict ocular analyte concentration.

37. The method of claim 34 wherein the data points comprise image perception.

38. The method of claim 37, including using an advanced multivariate image analysis to relate multiple backscattered signals to detect minute changes of refractive index.

39. The method of claim 34 wherein one or more acquired data points are selected and enhanced through digital image filtering while minimizing background noise and motion artifact.

40. The method of claim 34, including analyzing one or more data points using an image-based principal component analysis (PCA) and/or partial least squares (PLS) regression method.

41. The method of claim 34, wherein two or more acquired data points are compared using a correlation or differencing method.

42. The method of claim 34, including performing a score analysis on multiple data points and utilizing a multivariate image regression (MIR).

43. The method of claim 42, comprising performing MIR using a PLS or other suitable algorithm in order to form a calibration model that is capable of predicting analyte concentration.

44. The method of claim 43, comprising using a multivariate algorithm for prediction of a concentration of ocular analyte in both calibration and cross validation.

45. The method of claim 43, comprising using a multivariate algorithm based on one or more fiducial markers from one or more ocular structures of the eye.

46. The method of claim 43, comprising applying a principal component analysis to an acquired dataset comprised of at least two data points determined by analyzing one or more fiducial markers in an eye of the subject.

47. The method of claim 34, comprising:
    i) analyzing first and second principal components of at least one dataset of the data points, and
    ii) analyzing score plots of the first versus the second principal components from the dataset, wherein a shape or perception changes show that concentration relationships are captured within the first and second principal component factors.

48. The method of claim 47, further including:
    comparing at least one data point at one concentration with respect to another, and
    determining whether the similarity between the two data points is represented in the first component, while the second component shows where main dissimilarities occur.

49. The method of claim 34, wherein the stimulus wavelength is in the visible to near-infrared region of the electromagnetic spectrum.

50. The method of claim 49, further including generating the stimulus light energy at varying intensities, in order to compensate for any spatial variations in the subject's iris pattern due to an increase or decrease in the pupil diameter.

51. The method of claim 50, wherein the compensation is encoded into a partial least squares (PLS) calibration measurement.

52. The method of claim 49, wherein the light source is configured to provide a defined opto-stimulus protocol in which the stimulus light intensity is varied.

53. The method of claim 49, wherein the illumination source generates light in the near infrared light region (~700-1400 nm) to minimize corneal reflections and enhance the iris structures, and to increase the signal-to-noise ratio as scattering effects are also lessened.

54. The method of claim 34, wherein the ocular analyte comprises glucose.

55. The method of claim 34, wherein the stimulus and illumination wavelengths are different.

56. The method of claim 34, wherein the stimulus and illumination wavelengths are the same.

57. An in vivo method for measuring a physiological concentration of at least one ocular analyte in an eye of a subject, comprising:
    measuring at least light refraction from one or more fiducial markers in an eye of the subject using a sequential imaging method that is accompanied with a physiological calibration process, wherein at least one stimulus wavelength of light energy is used to maximize the subject's pupillary light reflex.

58. The method of claim 57, including using a bimodal illumination source with both stimulus and illumination wavelengths.

59. The method of claim 58, wherein the illumination source has a substantially uniform irradiance profile to minimize light intensity variations across the image to optimize the acquired image quality.

60. The method of claim 59, wherein the illumination source is in the near infrared light region and the stimulus wavelength is in the visible region.

61. The method of claim 60, including using the near infrared region to minimize corneal reflections to further enhance iris structures, thus increasing the signal-to-noise ratio.

62. The method of claim 58, wherein the illumination source has a glancing angle delivery.

63. The method of claim 58, wherein the stimulus and illumination wavelengths are different.

64. The method of claim 58, wherein the stimulus and illumination wavelengths are the same.

65. The method of claim 57, including using the at least one stimulus source of light at varying intensities in order to compensate for spatial variations in the iris pattern due to an increase or decrease in the pupil diameter.

66. The method of claim 65, wherein measured compensation is dynamically encoded into a regression technique with a partial least squares (PLS) calibration approach.

67. The method of claim 66, comprising using dynamic image data.

68. The method of claim 66, comprising using static image data.

69. The method of claim 57, wherein the calibration data relates the concentration to a dynamic image, $I(x,y,t)$, where t is time.

70. The method of claim 69, wherein dependent variable data are respective movies of the eye response to the light protocol which correspond to a given concentration.

71. The method of claim 57, including resolving prediction issues associated with acquiring measurements at different light levels which also have dependent pupillary responses.

72. The method of claim 71, including using Equation 2: $C=I(x,y,t)B+B_0$, wherein C is concentration, I is the dynamic image, and B and $B_0$ are the respective regression parameters.

73. The method of claim 57, wherein, by an iterative process of obtaining subsequent movie images at varying ocular analyte concentrations, a robust dynamic multivariate data set of data points at differing stimulus light intensity values and varying analyte concentrations is obtained and used for calibration.

74. The method of claim 73, wherein the data set is supplemented with one or more fiducial markers.

75. The method of claim 74, wherein the one or more fiducial markers comprises one or more of: pupil diameter, iris characteristics, or cross correlation values prior to ocular analyte calibration.

76. The method of claim 75, wherein the supplemental data is used to aid in obtaining accurate predictions.

77. The method of claim 57, including using a PCA/PLS-type model to include a dynamic aspect which includes a time-changing stimulus as a factor.

78. The method of claim 77, including detecting correlated movements that are caused by time lags or delays that cannot be seen in a static calibration model.

79. The method of claim 57, wherein the ocular analyte comprises glucose.

80. A method for determining concentration of an ocular analyte in a subject comprising:
   delivering an incident light to at least a portion of the subject's eye through a glancing angle delivery, and
   measuring refraction of the incident light with respect to a change in an index of refraction of two given media related to Equation I, $(\sin\theta_1)/(\sin\theta_2)=\eta_2/\eta_1$, wherein
   $\eta_1$ is the refractive index of the primary (incident) medium,
   $\eta_2$ is the refractive index of the secondary (transmitted) medium,
   $\theta_1$ is the angle that the incident light rays take with respect to the normal, and
   $\theta_2$ is angles that the light rays take with respect to the normal.

81. The method of claim 80, further including determining the refractive index changes with respect to one of the media.

82. The method of claim 80 including relating one or more data points to a pre-determined calibration model to predict ocular analyte concentration.

83. The method of claim 80 wherein the data points comprise image perception.

84. The method of claim 83, including using an advanced multivariate image analysis to relate multiple backscattered signals to detect minute changes of refractive index.

85. The method of claim 80 wherein one or more acquired data points are selected and enhanced through digital image filtering while minimizing background noise and motion artifact.

86. The method of claim 80, including analyzing one or more data points using an image-based principal component analysis (PCA) and/or partial least squares (PLS) regression method.

87. The method of claim 80, including performing a score analysis on multiple data points and utilizing a multivariate image regression (MIR).

88. The method of claim 87, comprising performing MIR using a PLS or other suitable algorithm in order to form a calibration model that is capable of predicting analyte concentration.

89. The method of claim 88, comprising using a multivariate algorithm for prediction of a concentration of ocular analyte in both calibration and cross validation.

90. The method of claim 88, comprising using a multivariate algorithm based on one or more fiducial markers from one or more ocular structures of the eye.

91. The method of claim 88, comprising applying a principal component analysis to an acquired dataset comprised of at least two data points determined by analyzing one or more fiducial markers in an eye of the subject.

92. The method of claim 91, comprising:
   i) analyzing first and second principal components of at least one dataset of the data points, and
   ii) analyzing score plots of the first versus the second principal components from the dataset, wherein a shape or perception changes show that concentration relationships are captured within the first and second principal component factors.

93. The method of claim 92, further including:
   comparing at least one data point at one concentration with respect to another, and
   determining whether the similarity between the two data points is represented in the first component, while the second component shows where main dissimilarities occur.

94. The method of claim 80, wherein the incident light is in the near infrared light region (~700-1400 nm) to minimize corneal reflections and enhance the iris structures, and to increase the signal-to-noise ratio as scattering effects are also lessened.

95. A system for determining concentration of an ocular analyte in a subject, comprising:
- a bimodal illumination source that emits at least one beam of non-collimated light, the beam being directed at one or more fiducial markers in the eye, such that at least a portion of the beam scattered or reflected by the one or more fiducial markers is refracted upon exiting the eye; and
- at least one data capturing module that receives at least one data point formed by the refracted beam, the data point comprising a perception of the one or more fiducial markers, and based on the perception of the one or more fiducial markers, the data capturing module correlates a level of ocular analyte in the eye with the one or more data points.

96. The system of claim 95, wherein the bimodal illumination source comprises varying intensities.

97. A method for determining concentration of an ocular analyte in a subject comprising:
- delivering an incident light from a bimodal light source to at least a portion of the subject's eye, and
- measuring refraction of the incident light with respect to a change in an index of refraction of two given media related to Equation I, $(\sin \theta_1)/(\sin \theta_2) = \eta_2/\eta_1$, wherein
  $\eta_1$ is the refractive index of the primary (incident) medium,
  $\eta_2$ is the refractive index of the secondary (transmitted) medium,
  $\theta_1$ is the angle that the incident light rays take with respect to the normal, and
  $\theta_2$ is angles that the light rays take with respect to the normal.

98. The method of claim 97, wherein the bimodal light source comprises varying intensities.

* * * * *